United States Patent [19]
Jinotti

[11] Patent Number: 5,346,478
[45] Date of Patent: Sep. 13, 1994

[54] PULMONARY CATHETER

[76] Inventor: Walter J. Jinotti, 10 Scott St., New Brunswick, N.J. 08903

[21] Appl. No.: 72,004

[22] Filed: Jun. 7, 1993

[51] Int. Cl.$^5$ ............................................. A61M 5/00
[52] U.S. Cl. .................................... 604/171; 604/163
[58] Field of Search ............... 604/171, 163, 164, 280, 604/283

[56] References Cited

U.S. PATENT DOCUMENTS

| | | | |
|---|---|---|---|
| 4,327,735 | 5/1982 | Hampson | 604/171 |
| 4,595,005 | 6/1986 | Jinotti | 604/32 |
| 4,805,611 | 2/1989 | Hodgkins | 604/171 |
| 5,061,246 | 10/1991 | Anapliotis | 604/171 |
| 5,217,439 | 6/1993 | McClusky | 604/163 |

FOREIGN PATENT DOCUMENTS 8302065  6/1983  PCT Int'l Appl. ................. 604/171

*Primary Examiner*—John G. Weiss
*Attorney, Agent, or Firm*—Robert A. Green

[57] ABSTRACT

The disclosure is of a pulmonary catheter assembly including a tube assembly for insertion into a patient for providing oxygen and suction thereto and a flexible sleeve enclosing said tube assembly. The sleeve is secured to one end of the tube assembly and extends toward and beyond the end which is inserted into the patient. The sleeve is inflatable to permit easy introduction of the tube assembly into the patient.

1 Claim, 2 Drawing Sheets

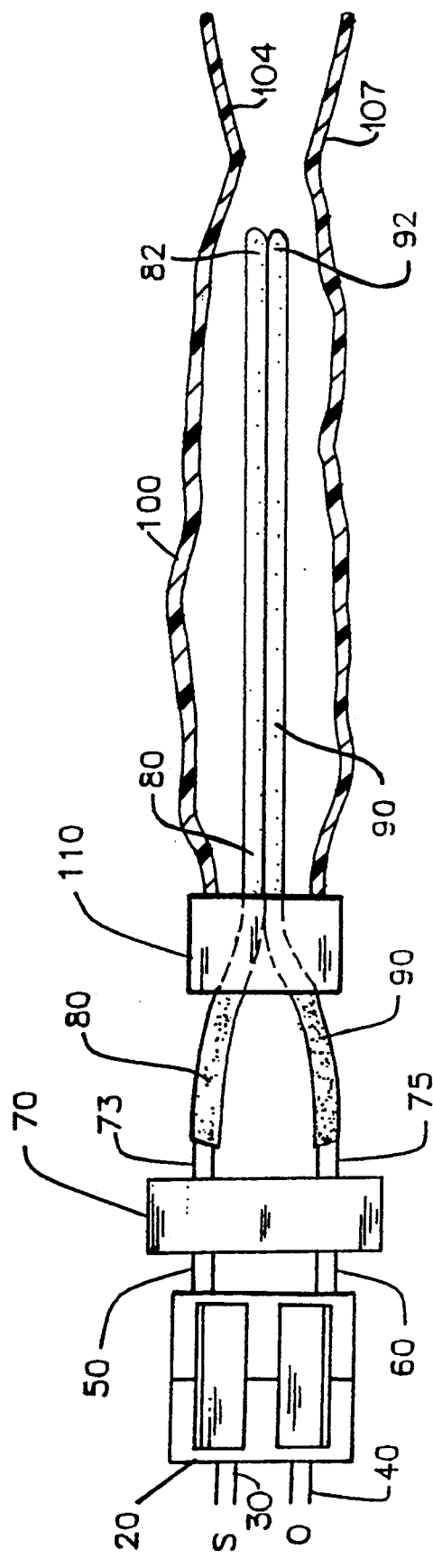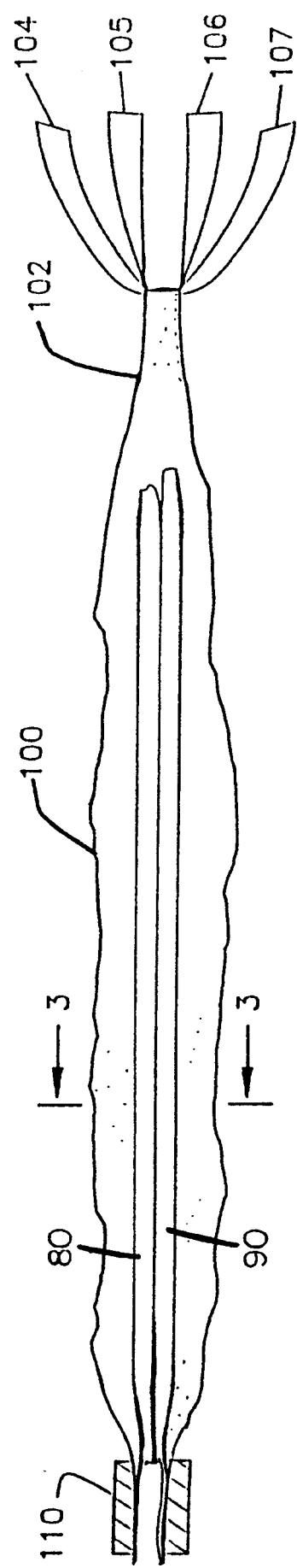
FIG. 1
FIG. 2

PULMONARY CATHETER

BACKGROUND OF THE INVENTION

Pulmonary catheters are in general use for suctioning mucus out of the lungs of a patient and for feeding oxygen or other substances into the lungs. Such catheters generally comprise a valve for controlling the flow of oxygen or suction and a tube assembly secured to the valve and operable to be fed into the lungs of a patient. One catheter presently in use is described and claimed in U.S. Pat. No. 4,595,005 of the present inventor and entitled DUAL-PURPOSE CATHETER.

When a catheter tube is inserted into a patient, the inserted end becomes coated with mucus which, when the tube is withdrawn, can touch the technician and expose him Co the mucus. If the patient has AIDS or some other communicable disease, the results could be disastrous to the technician.

Suggestions have been made for providing a catheter having means for protecting the user but none is satisfactory for the intended purpose.

SUMMARY OF THE INVENTION

The present invention includes a catheter assembly having one or more tubes adapted to be inserted into a patient and having a flexible sleeve secured to the end of the tubes which are not inserted into the patient. The sleeve can be manipulated to permit the catheter tubes to be introduced into the patient and removed back into the sleeve without touching the user.

DESCRIPTION OF THE DRAWINGS

FIG. 1 is side elevational view of a catheter assembly embodying the invention;

FIG. 2 shows the assembly of FIG. 1 as it appears when ready for insertion into a patient.

DESCRIPTION OF THE INVENTION

Figure 3:
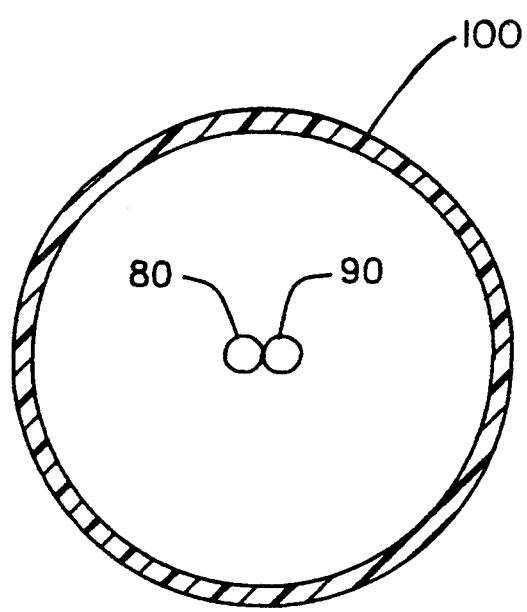
FIG. 3 is a sectional view along the lines 3—3 in FIG. 2 showing a portion of the apparatus of the invention.

A catheter assembly 10 embodying the invention may be of the type shown in the above identified Jinotti patent which is incorporated herein by reference. The catheter assembly includes a dual-function valve 20 for coupling suction or oxygen to a patient. The valve includes an input tube 30 coupled to an oxygen supply (not shown) and an input tube 40 coupled to a suction source (not shown). The valve 20 also includes two output tubes 50 and 60 to which an adapted 70 may be coupled if desired. The preferred adapter is shown and claimed in U.S. Pat. No. 4,995,387 which is incorporated herein by reference.

In practicing the invention, a single tube or lumen or a double tube may be attached to the valve 20. Two lumens 80 and 90 are shown and described. The tubes 80 and 90 have valve ends which are secured to outlet tubes 73 and 75 on the adapter 70. The tubes also have patient ends 82 and 92 which are inserted into a patient. Normally, the tubes 80 and 90 are secured together along most of their lengths to form a unitary assembly which is easy to handle.

According to the invention, a protective sleeve 100 is provided enclosing the tubes 80 and 90 and extending from the valve ends thereof to beyond the patient ends 82 and 92 thereof. The sleeve 100 is thin and flexible and is made of a suitable plastic.

The sleeve extends perhaps three to four inches beyond the patient ends of the tubes 80 end 90 and has a diameter which is considerably greater than the widths of the tubes 80 and 90 for a purpose to be described.

The sleeve is secured in air-tight engagement to the adapter ends of the tubes 80 and 90 by means of adhesive tape 110 or with any other suitable means.

Two pairs of ties 104,105, 106 and 107, of the same material as the sleeve 100, extend from the patient end of the sleeve and are of any convenient length to permit them to be tied to a piece of equipment adjacent to the operator's work area. These ties may be four or five inches long or so.

In using the invention, the operator grasps the end 102 of the sleeve 100 and closes this open end. He then introduces oxygen through valve 20 to inflate the sleeve and to cause it to surround and be spaced from the tubes 80 and 90, perhaps three inches or so as shown in FIG. 3. The operator can then release the end of the sleeve, which remains inflated sufficiently, to permit him to introduce the tubes 80 and 90 into a patient. If the catheter tubes having been introduced directly into the patient, there is no need to use the ties 104, 105, 106 and 107. If an incubation tube is in the patient and the catheter tubes are introduced through the incubation tube, the ties can be secured to the incubation tube.

After the desired procedure has been completed, the operator withdraws the tubes from the patient, allows their entire lengths to enter the sleeve, and the tube assembly can be removed from the valve and discarded. Alternatively, the tube assembly can be re-introduced into the patient and used again one or more times. It can be seen that the entire operation is performed without the operator being exposed to mucus or other substances.

What is claimed is:

1. A pulmonary catheter assembly comprising
   a tube assembly adapted to be inserted into the mouth of a patient,
   said tube assembly having a first end to be inserted into a patient and a second end remote therefrom, and
   a flexible sleeve enclosing said tube assembly, said sleeve having a first patient end and a second end remote therefrom, said sleeve having its second end secured in air-tight engagement to said second end of said tube assembly and extending therefrom to several inches beyond said patient end of said tube assembly, said sleeve being inflatable like a balloon with the introduction of a gas into said first end thereof when said tube assembly is to be inserted into a patient, said sleeve having a considerably larger diameter than said tube assembly when inflated, said tube assembly being completed enclosed in said sleeve when it is withdrawn from a patient without exposure of an operator of said tube assembly thereto and to any substances which might be thereon, and
   a plurality of ties secured to said first end of said sleeve for tying said sleeve in place during operation on a patient.

* * * * *